United States Patent

Nakagawa et al.

[11] Patent Number: 6,134,943
[45] Date of Patent: Oct. 24, 2000

[54] ELECTRON CAPTURE DETECTOR FOR GAS CHROMATOGRAPH

[75] Inventors: Kazuya Nakagawa; Hiroyuki Tsujiide, both of Kyoto, Japan

[73] Assignee: Shimadzu Corporation, Kyoto, Japan

[21] Appl. No.: 09/163,141

[22] Filed: Sep. 29, 1998

[30] Foreign Application Priority Data

Oct. 3, 1997 [JP] Japan .................................. 9-287946

[51] Int. Cl.$^7$ .................................................. G01N 27/66
[52] U.S. Cl. ........................................ 73/23.35; 73/23.41
[58] Field of Search ................................. 73/23.22, 23.35, 73/23.41

[56] References Cited

U.S. PATENT DOCUMENTS 5,804,828  9/1998  Abdel-Rahman .................. 250/381

Primary Examiner—Daniel S. Larkin
Attorney, Agent, or Firm—Majestic, Parsons, Siebert & Hsue P.C.

[57] ABSTRACT

An electron capture detector has a detection cell containing an electrode and a radioactive isotope for ionizing a carrier gas and causing electrons to be emitted. Before the detection cell begins to be contaminated, a pulse voltage is applied to the electrode and the frequency of this pulse voltage is controlled by a loop control routine to find an initial pulse frequency value such that a current through the electrode due to the emitted electrons comes to have a specified current value as a carrier gas is introduced into the detection cell. When a sample is analyzed after the detection cell becomes contaminated, the same process is carried out before the sample is injected and a pre-measurement pulse frequency value is obtained. After the sample is injected, the same process is repeated to obtain a measured pulse frequency value. The concentrations of components of the sample are calculated from the measured pulsed frequency value, and the effects of contamination of the detection cell are removed by considering both the initial and pre-measurement pulse frequency values.

17 Claims, 2 Drawing Sheets

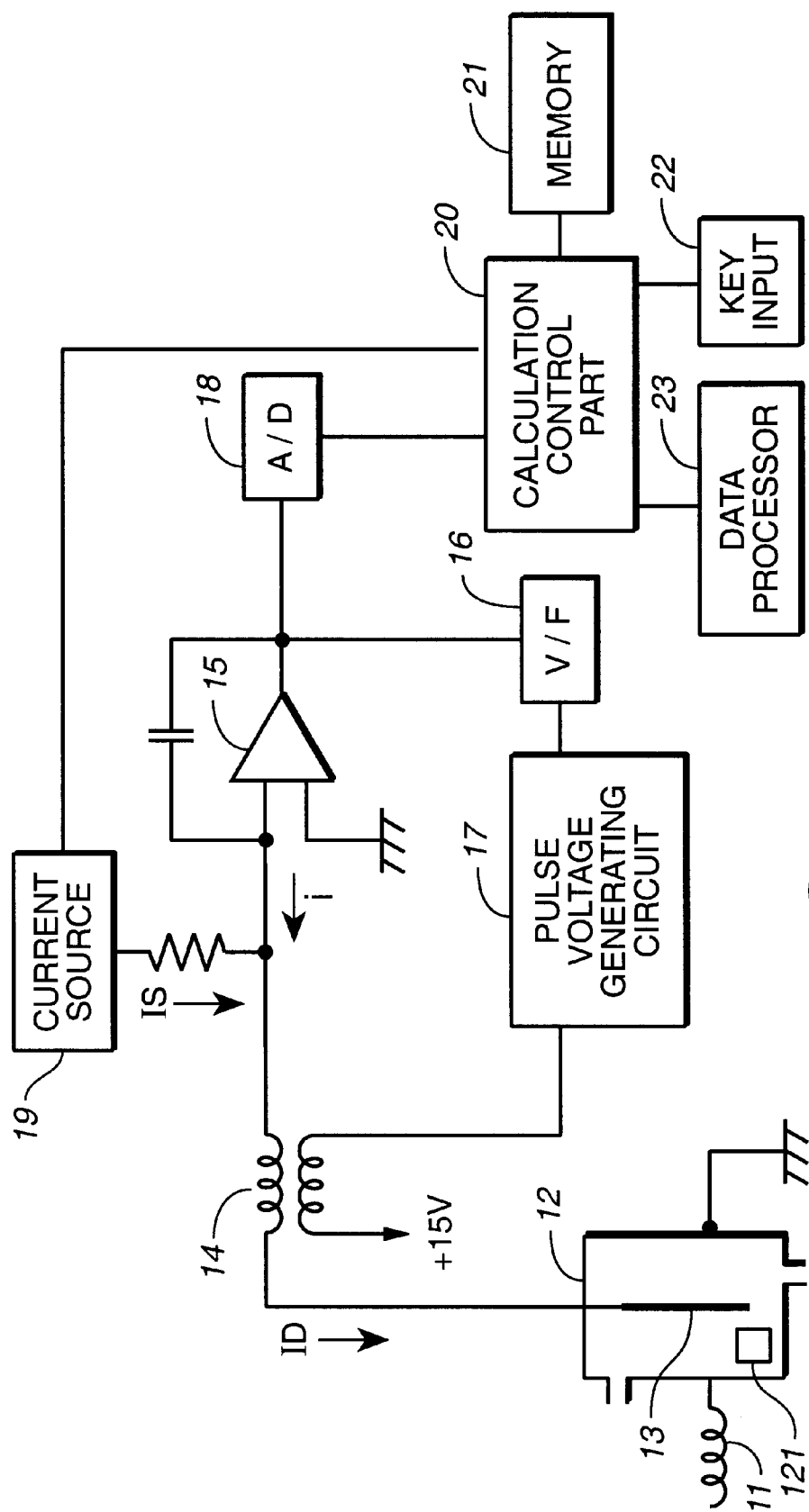
FIG._1

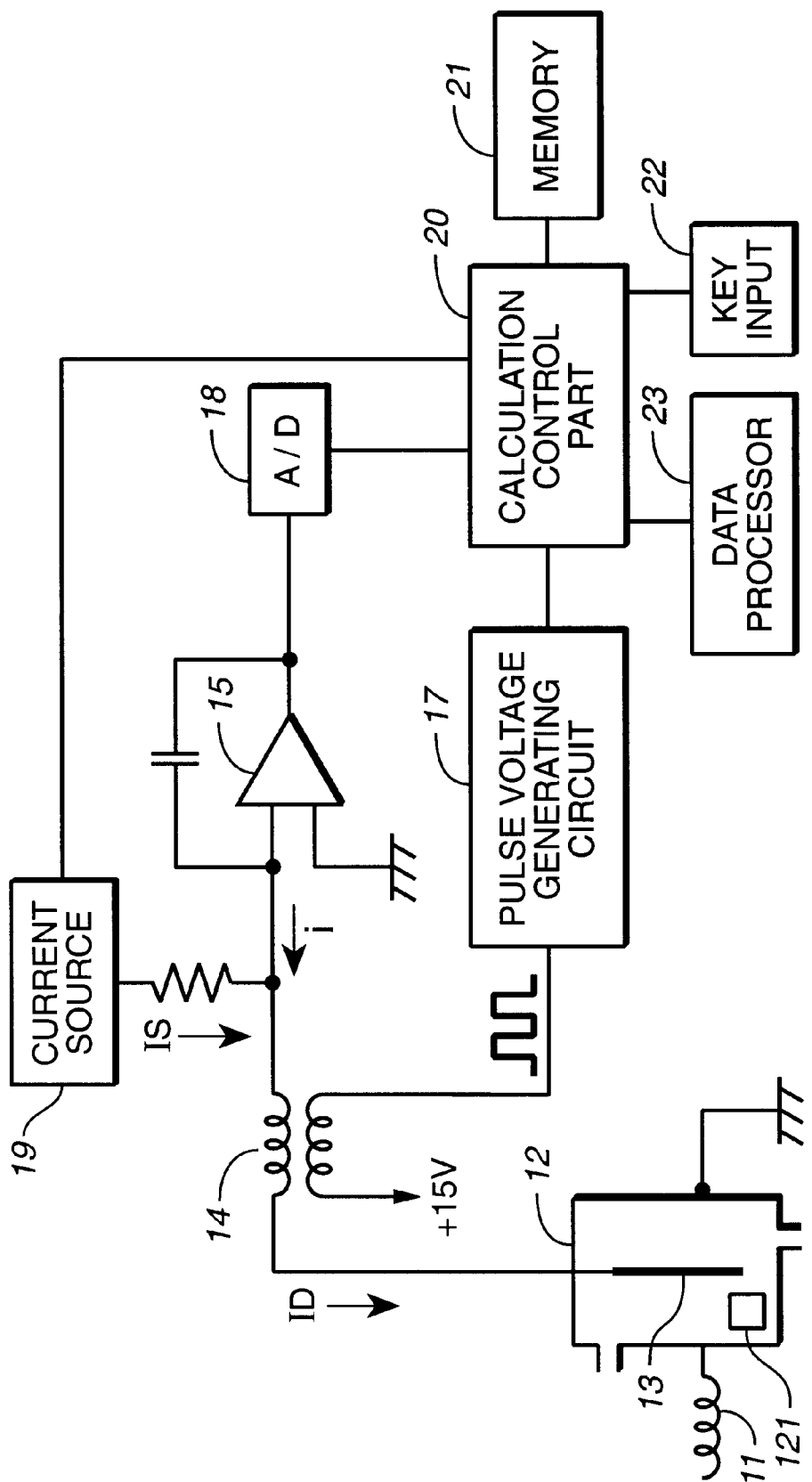
FIG._2

ELECTRON CAPTURE DETECTOR FOR GAS CHROMATOGRAPH

BACKGROUND OF THE INVENTION

This invention relates to an electron capture detector adapted to be used for a gas chromatograph.

Among the different kinds of detectors used for a gas chromatograph, electron capture detectors are useful for the detection of compounds tending to combine with electrons, such as halogens and nitro compounds. For this reason, electron capture detectors are commonly used for the detection of residual amounts of organic mercury, agricultural chemicals, and PCBS, as well as very small amounts of steroids and amino acids, by converting them into a derivative with a tendency to combine with electrons.

To briefly explain the principles of operation of an electron capture detector, a radioactive isotope such as $^{63}Ni$ is sealed inside a detection cell, and a carrier gas is introduced such that its molecules are ionized by the radiation from the isotope, free electrons being thereby emitted. If a voltage is then applied to a positive electrode disposed inside this detection cell, a certain current will flow through the electrode due to these free electrons under a steady condition. If a pulsed voltage is applied to the electrode and the difference between the pulse current which flows through the electrode as a result of this pulsed voltage and a specified current $I_S$ is inputted to an integrator, the output from this integrator is a voltage which depends on the difference between the average value of the pulse current (the pulse current per unit time) and the specified current $I_S$. If this output from the integrator is introduced into a voltage-frequency converter to obtain therefrom a pulse signal with frequency depending on the difference between these two currents and a pulse voltage is generated based thereon, the frequency f of the pulse voltage applied to the electrode in a steady state takes a value depending on the specified current $I_S$.

If molecules of an electron-capturing substance are introduced into the detection cell, these molecules serve to capture the free electrons emitted from the carrier gas, causing the density of the free electrons to be reduced. Since the negative ions which have captured the free electrons move much more slowly than the free electrons, the current which flows through the electrode also diminishes due to this decrease in the density of the free electrons. This causes the output voltage from the integrator to grow larger, and the frequency f of the pulse signal outputted from the voltage-frequency convertor increases. In other words, the number of pulses which are generated per unit time increases so as to make up for the decrease in the number of electrons captured by each pulsed voltage.

It is known that the density a of an electron-capturing substance and the pulse frequency, f are related as follows:

$$Kf = (k_1 a + K_D) \quad (1)$$

where $Kf$, $k_1$, and $K_D$ are constants. (See, for example, R. J. Maggs, et al.; "The Electron Capture Detector—A Mode of Operation", Analytical Chemistry, Vol. 43, No. 14, December (1971) 1967.) Thus, the change in the pulse frequency $\Delta f$ from the situation where a=0 (that is, where no electron-capturing substance has been introduced into the detection cell) is proportional to the density a, being given by:

$$\Delta f = (k_1 a + K_D)/K - K_D/K = (k_1/K)a \quad (2)$$

In other words, the density a of the sample can be calculated from the change in the frequency $\Delta f$ as follows:

$$a = \Delta f/(k_1/K) \quad (3)$$

where the value of $(k_1/K)$ is understood to be preliminarily determined experimentally. Since the output voltage V from the integrator depends on the change in the pulse frequency f, a chromatogram of a target electron-capturing substance can be obtained by recording this output voltage V with an elapse of time.

As measurements are repeated and the electrode and the interior of the detection cell become polluted by samples, it becomes difficult for the current to flow and the frequency f tends to increase. In other words, even if a same sample is measured, the result of measurement will tend to change with time. Another problem which is associated with the use of a radioactive isotope is that the interior of the detection cell cannot be washed easily because it requires a special technology.

SUMMARY OF THE INVENTION

It is therefore an object of this invention, in view of the above, to provide an improved electron capture detector capable of appropriately correcting the effects of time-dependent changes due, for example, to the pollution inside the detection cell and hence of always outputting a reliable result of measurement.

An electron capture detector embodying this invention, with which the above and other objects can be accomplished, may be characterized as comprising not only a detection cell with electron emitting means (or ionizing means, such as a radioactive isotope) for ionizing a carrier gas being introduced thereinto and thereby causing electrons to be emitted, but also a current value setting means (or an input means) for allowing a user to specify a current value, a pulse control means for applying a pulse voltage to an electrode inside the detection cell and controlling the frequency value of the pulse voltage such that a current due to the emitted electrons has the specified current value, and a memory means for storing measured data, such as frequency values.

By the "initial condition" will be meant the condition under which the detection cell may be considered clean and not contaminated, say, immediately after the electron capture detector was produced or was cleaned. Under this condition, the pulse frequency $f_{00}$ corresponding to a specified current value is measured, and this measured value (referred to as "the initial frequency") is stored in the memory means. When a sample is to be analyzed after the detector has been in use and the detector cell may no longer be considered clean, the pulse frequency $f_0$ corresponding to the specified current is measured before the sample is injected, and this measured frequency value is also stored in the memory means. These two values may be utilized according to this invention in different ways to carry out an accurate measurement by taking into account the contaminated condition of the detection cell.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a schematic block diagram of an electron capture detector embodying this invention; and FIG. 2 is a schematic block diagram of another electron capture detector embodying this invention.

Throughout herein, like or equivalent components are indicated by the same numerals even where they are components of different devices and may not necessarily be described repetitiously.

DETAILED DESCRIPTION OF THE INVENTION

The invention is described next by way of an example shown in FIG. 1 which schematically shows the structure of an electron capture detector embodying this invention, wherein numeral 12 indicates a grounded detection cell connected to a gas chromatograph column 11, being a sealed structure with an inlet and an outlet for a carrier gas and containing therein a beta-ray source 121 comprising a radioactive isotope such as $^{63}$Ni and an anode 13. The anode 13 is connected to the secondary coil of a transformer 14 and to a differential amplifier 15 through this coil. The output voltage of this differential amplifier 15 is applied to a voltage-frequency (V/F) converter 16, and the voltage-frequency converter 16 outputs a pulse signal with frequency which depends on the inputted voltage. The pulse signal from the voltage-frequency converter 16 is received by a pulse voltage generating circuit 17 which serves to output a voltage with this frequency to the primary coil of the transformer 14. The output voltage from the differential amplifier 15 is also converted into a digital signal by an analog-to-digital (A/D) converter 18 and is transmitted to a current source part 19 and a calculation control part 20. A memory 21, a key input part 22 (or the "input means"), and a data processor 23 are connected to the calculation control part 20.

When a carrier gas is caused to flow into the detection cell 12, the carrier gas molecules are ionized by the beta-ray source and emit free electrons with low kinetic energies. Since a positive pulse voltage is applied to the anode 13 from the secondary coil of the transformer 14, a current flows through the anode 13 due to these free electrons while this positive voltage is on the anode 13. If the frequency f of the pulse voltage is increased, the average current $I_D$ through the anode 13 over a specified period of time longer than the period of the pulse increases. Likewise, if the frequency f is reduced, the average anode current $I_D$ decreases.

If a specified value of current $I_S$ is inputted through the key input part 22, the calculation control part 20 responds by outputting a corresponding current setting signal to the current source part 19, causing the current source part 19 to output a current with the specified current value $I_S$. Since the value of the anode current $I_D$ is determined by the pulse frequency f, as explained above, the difference $i=I_D-I_S$ is derived from the differential amplifier 15, as shown in FIG. 1. A voltage which corresponds to this difference i is outputted from the differential amplifier 15 and applied to the voltage-frequency converter 16. The voltage-frequency converter 16 outputs a pulse signal of a frequency corresponding to this inputted voltage, and the pulse voltage generating circuit 17 applies a voltage of this frequency to the primary coil of the transformer 14. The transformer 14 with its primary and secondary coils, the differential amplifier 15, the voltage-frequency converter 16, and the pulse voltage generating circuit 17 may together be referred to as the pulse control means for applying the pulse voltage with a frequency obtained by a loop control routine as described above. Since the voltage-frequency converter 16 is set such that the pulse frequency f is increased if the difference i is greater than a specified value (such as zero), the frequency f is controlled by this loop control such that the difference i will approach a specified value. The value of the pulse frequency when the difference i is controlled to have the specified value is herein referred to as "the zero frequency".

According to the present invention, the key input part 22 is operated after the detection cell 12 is cleaned, and the zero frequency thus obtained is stored in the memory 21 as "the initial frequency $f_{00}$".

Whenever a user uses this electron capture detector thereafter to analyze a sample, the key input part 22 is operated before the sample is introduced into the detection cell 12 and the zero frequency $f_0$ is similarly measured and stored in the memory 21 as the pre-measurement frequency. Since the interior of the detection cell 12 continues to be contaminated by the samples, it becomes harder for the anode current to flow, as the detector continues to be used. In other words, the pre-measurement frequency tends to increase with the number of times the detector is used.

After the zero frequency $f_0$ is stored as the pre-measurement frequency, the sample is introduced from the column 11 into the detection cell 12. The sample captures the free electrons inside the detection cell 12 as explained above and thereby causes the anode current $I_D$ to become weaker. At the same time, the pulse frequency increases in order to adjust the value of the difference i. Let f be the value to which the pulse frequency increases.

According to one of the methods embodying this invention, it is not the frequency value f thus measured that is directly used to calculate the sample density a from Formula (3) given above. Instead, the initial frequency $f_{00}$ and the pre-measurement frequency $f_0$, which are stored in the memory 21, are consulted to estimate what the measured frequency would have been if the detection cell 12 had been clean. Such an estimated frequency value will be written as $f_1$, and it is assumed that the fractional change of the measured frequency (f to $f_1$) due to the contamination of the detection cell 12 is the same as between the two zero frequencies $f_{00}$ and $f_0$, that is:

$$f_1/f = f_{00}/f_0 \qquad (4)$$

If the estimated (corrected) frequency $f_1$ is used instead of the measured frequency value f in Formula (3), one obtains:

$$a = \Delta f/(k_1/K) = (f_1-f_0)/(k_1/K) \qquad (5)$$

or, if the values $f_{00}$, $f_0$, and f are directly used, $$a = \{f(f_{00}/f_0)-f_0\}/(k_1/K) \qquad (6)$$

This may be explained in another way as follows. As the interior of the detection cell 12 becomes contaminated, the constant K in Formula (1) changes, say, to another constant $K_1$ such that Formula (1) changes as follows:

$$K_1 f = (k_1 a + K_D) \qquad (1')$$

Thus, the zero frequency corresponding to a=0 when the detection cell 12 is clean is $f_{00}=K_D/K$ but it is given from (1') as $f_0=K_D/K_1$ when the detection cell 12 has become contaminated. Thus, $$f_{00}/f_0 = K_1/K \qquad (7)$$

and Formula (2) becomes, when the detection cell 12 is contaminated, $$\Delta f_1 = f_1-f_0 = (k_1/K_1)a = (f_0/f_{00})(k_1/K)a = (f_0/f_{00})\Delta f \qquad (8)$$

This means, as shown in Formulas (5) and (6), that the sample density a can always be calculated by the same formula by replacing f by $f_1=(f_0/f_{00})f$.

The zero frequency values (inclusive of the aforementioned initial frequency and pre-measurement frequency $f_{00}$ and $f_0$) may be stored in the memory 21 either manually through the key input part 22 or automatically at a specified timing. For example, as the detection cell 12 is heated at the time of an analysis, the zero frequency value may be caused to be stored automatically when the temperature of the detection cell 12 reaches a specified level. If the zero frequency values are thus stored sequentially in the memory 21, the oldest value stored may be treated as the initial frequency $f_{00}$ and the most recently stored value as the pre-measurement frequency $f_0$.

Alternatively, Formula (8) may be rewritten as:

$$f_1 - f_0 = (f_0/f_{00})\Delta f = c\,\Delta f \tag{9}$$

where $c = f_0/f_{00}$. After the detection cell 12 is washed, it is contaminated gradually in a controlled manner. Values of $f_0$ are obtained at different levels of contamination, and the corresponding values of $c = f_0/f_{00}$ are stored in the memory 21. At the time of an actual analysis, if the pre-measurement frequency $f_0$ is obtained by a preliminary measurement, the corresponding value of c can be read out from the memory 21 and the desired sample concentration a can be calculated from Formulas (9) and (5).

By all of the methods described above, it is required that the specified current $I_S$ must be the same between the time of the analysis and when the value of $f_{00}$ is stored immediately after the detection cell 12 is washed. Since the value of the specified current $I_S$ varies, depending on the sample to be analyzed, values of the initial and pre-measurement frequencies $f_{00}$ and $f_0$ must generally be stored for different values of the specified current $I_S$. A method of simplifying this process is explained next.

According to Maggs, et al. cited above, $$I_D = bq\{1 - \exp(-(K_D + ak_1)/f)\}/\{(K_D + ak_1)/f\}$$

where b is a constant and q is the electronic charge. If it is assumed that f is sufficiently small, $$I_D = bqf/(K_D + ak_1)$$

and if a=0, $$I_D = bqf_0/K_D.$$

If the value of $f_0$ when the anode current $I_D$ is equal to $I_S$ is written as $f_{0S}$, $$I_S = bqf_{0S}/K_D,$$

or the zero frequency corresponding to the arbitrary current value $I_S$ is:

$$f_{0S} = (I_S/I_D)f_0.$$

Thus, if the difference in frequency when the detection cell is contaminated and the anode current is $I_S$ is written as $\Delta f_{1S}$, one obtains from Formula (8):

$$\Delta f_{1S} = (f_{0S}/f_{00})\Delta f = (I_S/I_D)(f_0/f_{00})\Delta f = (I_S/I_D)c\,\Delta f.$$

The sample concentration a can be obtained by thus calculating $\Delta f_{1S}$.

In summary, a correct sample concentration value can always be obtained by an electron capture detector of this invention even after the detection cell has become contaminated. The value of the current zero frequency $f_0$ is stored in the memory 21, but this is a value corresponding to the degree of contamination at the time of the measurement. Thus, a warning device may be provided for outputting a warning signal to the data processor 23, for example, when this value exceeds a specified threshold value, urging the user to clean the detection cell 12. Since the memory 21 also stores the initial frequency $f_{00}$ immediately after the detection cell 12 is washed, the current zero frequency value can be compared therewith and a threshold value may be specified preliminarily in terms of the difference or the ratio therebetween (such as $f_{00}/f_0 = 0.5$).

As a variation, the functions of the voltage-frequency converter 16 may be carried out by the calculation control part 20, as shown in FIG. 2. In this case, the output from the differential amplifier 15 is received through the A/D converter 18 by the calculation control part 20 which generates a pulse signal based on the received value and outputs the generated pulse signal to the pulse voltage generating circuit 17. This embodiment is advantageous in that all operations can be controlled from the key input part 22 of the calculation control part 20 and hence the operational efficiency of the detector improves. The calculation control part 20 according to this embodiment can also control the calculation of a current value corresponding to a detected pre-measurement frequency $f_0$ and transmission of a current-setting signal to the current setting part 19.

In summary, all modifications and variations of the embodiments described above, which are obvious to a person skilled in the art, are intended to be within the scope of this invention.

What is claimed is:

1. An electron capture detector comprising:
    a detection cell containing an electrode;
    ionizing means for ionizing a carrier gas introduced into said detection cell and thereby causing electrons to be emitted;
    a current source for outputting a specified current with a specified current value;
    pulse control means for applying a pulse voltage having a pulse frequency to said electrode to thereby cause the emitted electrons to flow through said electrode as an electrode current and controlling said pulse frequency such that said electrode current will have said specified current value; and
    memory means for storing an initial value of said pulse frequency controlled by said pulse control means when said detection cell is in an initial condition in which said detection cell is considered clean and a pre-measurement value of said pulse frequency controlled by said pulse control means before a sample to be analyzed is introduced into said detection cell.

2. The electron capture detector of claim 1 wherein said pulse control means includes:
    a transformer having a primary coil and a secondary coil, said secondary coil being connected to said electrode;
    a differential amplifier connected to said secondary coil for outputting a voltage corresponding to the difference between current value of said electrode current and said specified current value;
    a voltage-frequency converting means for receiving the voltage from said differential amplifier and thereby outputting a pulse signal with frequency which depends on the received voltage; and
    a pulse voltage generating means for outputting a voltage with the frequency of said pulse signal to said primary coil.

3. The electron capture detector of claim 1 wherein said pulse control means controls said pulse frequency by a loop control routine.

4. The electron capture detector of claim 2 wherein said pulse control means controls said pulse frequency by a loop control routine.

5. The electron capture detector of claim 1 further comprising a calculation controller which analyzes a sample introduced into said detection cell from a measured frequency value before said sample is introduced into said detection cell and said initial value of said pulse frequency and said pre-measurement value which are stored in said memory means.

6. The electron capture detector of claim 3 further comprising a calculation controller which analyzes a sample introduced into said detection cell from a measured frequency value before said sample is introduced into said detection cell and said initial value of said pulse frequency and said pre-measurement value which are stored in said memory means.

7. The electron capture detector of claim 5 wherein said calculation controller includes said voltage-frequency converting means.

8. The electron capture detector of claim 6 wherein said calculation controller includes said voltage-frequency converting means.

9. The electron capture detector of claim 5 wherein said calculation controller further serves to make a comparison between said initial value and said pre-measurement value and to output a warning signal based on a result of said comparison.

10. The electron capture detector of claim 6 wherein said calculation controller further serves to make a comparison between said initial value and said pre-measurement value and to output a warning signal based on a result of said comparison.

11. The electron capture detector of claim 5 further comprising an input means for causing said specified current value to be specified.

12. The electron capture detector of claim 6 further comprising an input means for causing said specified current value to be specified.

13. A method of gas chromatographic analysis, comprising the steps of:
   connecting an electron capture detector to a column of a gas chromatograph, said electron capture detector having a detection cell containing an electrode and ionizing means for ionizing a carrier gas introduced thereinto and thereby causing electrons to be emitted;
   specifying a current value;
   obtaining an initial pulse frequency value at an initial time, when said detection cell is considered clean, by introducing a carrier gas into said detection cell to cause electrons to be emitted therefrom, applying a pulse voltage having a pulse frequency to said electrode to cause the emitted electrons to flow through said electrode as an electrode current, and controlling said pulse frequency by a loop control routine such that said electrode current will have said specified current value;
   obtaining similarly a pre-measurement pulse frequency value before a sample is injected into a carrier gas flowing into said column;
   obtaining similarly a measured pulse frequency value after obtaining said pre-measurement pulse frequency value and an injected sample is introduced into said column; and
   analyzing components of said sample not only from said measured pulse frequency but also from said initial pulse frequency value and said pre-measurement pulse frequency by taking into account effects of changed conditions inside said detection cell.

14. The method of claim 13 wherein said loop control routine is carried out by a pulse control means which includes:
   a transformer having a primary coil and a secondary coil, said secondary coil being connected to said electrode;
   a differential amplifier connected to said secondary coil for outputting a voltage corresponding to the difference between current value of said electrode current and said specified current value;
   a voltage-frequency converting means for receiving the voltage from said differential amplifier and thereby outputting a pulse signal with frequency which depends on the received voltage; and
   a pulse voltage generating means for outputting a voltage with the frequency of said pulse signal to said primary coil.

15. The method of claim 13 further comprising the step of storing said initial pulse frequency value and said pre-measurement pulse frequency value in a memory means for storing data.

16. The method of claim 13 further comprising the steps of similarly obtaining a series of pre-measurement pulse frequency values without introducing any sample into said detection cell and by causing contamination of said detection cell in a controlled manner and storing the obtained pre-measurement pulse frequency values in a memory means for storing data.

17. The method of claim 13 wherein the steps of obtaining said initial pulse frequency value and said pre-measurement pulse frequency value are carried out by similarly obtaining a series of pre-measurement pulse frequency values consecutively without introducing any sample into said detection cell and the identifying the earliest obtained one of said pre-measurement pulse frequency values as said initial pulse frequency value and identifying the one of said pre-measurement pulse frequency values obtained immediately before the injected sample is introduced into said detection cell as said pre-measurement pulse frequency value.

* * * * *